United States Patent [19]

Hirschbuehler et al.

[11] Patent Number: 4,533,686

[45] Date of Patent: Aug. 6, 1985

[54] CURABLE EPOXY RESIN COMPOSITIONS

[75] Inventors: Kevin Hirschbuehler; Samuel E. Susman, both of Bel Air, Md.

[73] Assignee: American Cyanamid Co., Stamford, Conn.

[21] Appl. No.: 518,875

[22] Filed: Aug. 1, 1983

[51] Int. Cl.$^3$ ............................................. C08K 3/04
[52] U.S. Cl. ................................... 523/468; 525/407; 525/504; 525/523; 528/124; 528/365
[58] Field of Search ................ 523/468; 525/504, 407, 525/523; 528/124, 365

[56] References Cited

U.S. PATENT DOCUMENTS

| | | | |
|---|---|---|---|
| 3,763,087 | 10/1973 | Holub et al. | 523/468 |
| 3,932,360 | 1/1976 | Cerankowski et al. | 260/77.5 AM |
| 4,026,831 | 5/1977 | Moriya et al. | 528/114 |
| 4,107,128 | 8/1978 | Hosoi et al. | 523/468 |
| 4,374,214 | 2/1983 | Holub et al. | 523/466 |
| 4,410,664 | 10/1983 | Lee | 525/504 |

FOREIGN PATENT DOCUMENTS

| | | | |
|---|---|---|---|
| 52-74655 | 6/1977 | Japan | 523/468 |
| 1017612 | 1/1966 | United Kingdom . | |
| 1024288 | 3/1966 | United Kingdom . | |
| 1182377 | 2/1970 | United Kingdom . | |

OTHER PUBLICATIONS

Gillhan et al., Organic Coatings and Applied Polymer Science Proceedings, vol. 46, pp. 592–598, Mar.–Apr. 1982, and pp. 566–570, Mar. 1983.
A.C.S. Symposium Series #114, 1979, p. 157.

*Primary Examiner*—Lewis T. Jacobs
*Attorney, Agent, or Firm*—Steven J. Hultquist

[57] ABSTRACT

Curable compositions comprising epoxide prepolymers and polyaminobenzoates, alone, or combined with reinforcements, e.g., graphite fibers, and, optionally modified with second resins. The cured resin fiber matrix compositions exhibit high toughness combined with excellent hot/wet strength.

6 Claims, 3 Drawing Figures

CURABLE EPOXY RESIN COMPOSITIONS

FIELD OF THE INVENTION

This invention relates to improved epoxy resin compositions. In addition, it relates to curable epoxy resin compositions comprising reinforcing filaments and epoxy prepolymers combined with aromatic polyamine curing agents.

CROSS REFERENCE

The following concurrently filed applications are related:

| Serial No. | Applicant(s) |
|---|---|
| 518,87 | R. P. Krieger, Jr. |
| | K. Hirschbuehler |
| | R. P. Politi |
| 518,872 | D. W. Wang |
| | J. L. Courter |
| | D. K. Kohli |
| 518,863 | D. K. Kohli |
| 518,873 | K. Hirschbuehler |
| 518,874 | K. Hirschbuehler |
| | D. K. Kohli |
| 518,879 | D. R. Draney |
| | D. K. Kohli |
| 518,856 | D. W. Wang |
| | D. R. Draney |
| 518,875 | K. Hirschbuehler |
| | S. E. Susman |

BACKGROUND OF THE INVENTION

Epoxy resin compositions are useful to encapsulate electronic components, and as structural adhesives, and the like. Reinforced epoxy resin composites having high strength to weight ratios have found extensive use in the aircraft and aerospace industries, and in other applications where strength, corrosion resistance and light weight are desirable. For instance, fiber resin matrix materials have replaced aluminum and other metals in primary and secondary structures of modern military and commercial aircraft. Sporting equipment such as tennis rackets and golf clubs have also adopted fiber resin materials successfully.

Epoxy resin compositions and fiber modifications are abundant. Since the advent of fiber resin matrix materials, much effort has been expended in improving their properties and characteristics, including the development of many different curing systems.

Amine and polyamine curing agents have received wide acceptance, but the toxicity, low solubility, high exotherm and variable curing rates seen with the most commonly used amines, such as m-phenylenediamine, 4,4'-diaminodiphenyl methane and 4,4'-diaminodiphenyl sulfone, has made further improvement desirable. In particular, for aircraft structural applications, epoxy resins cured with available curing agents are either too brittle or do not have sufficient strength and stiffness under hot/wet conditions. It is disclosed in U.K. Pat. No. 1,182,377, which is incorporated herein by reference, that certain aromatic polyamines are effective as curing agents for a variety of polyepoxides, and the resulting cured compositions are useful as films, moldings, coatings and glass-reinforced laminates. There is no indication in the properties presented in the U.K. patent that the curing agents exemplified therein will produce the combination of toughness and strength under hot/wet conditions essential for use in the above-mentioned structural applications.

In U.S. Pat. No. 3,932,360, diamine cured polyurethane products are described, in which the diamines are of the formula, e.g.,

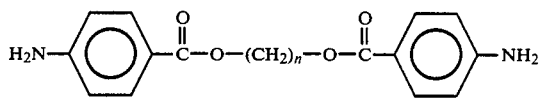

wherein n is an integer from 2 to 12. This '360 patent does not deal with curing compounds having more than one epoxide group per molecule.

In Gillhan et al, Organic Coatings and Applied Polymer Science Proceedings, Vol. 46, p. 592–598, March-April, 1982, polyepoxides cured with diamines of the immediately preceding formula (n is 3), are described.

The present development relates to curable epoxy resin compositions. In one of its aspects, it provides fiber resin matrixes comprising reinforcing filaments in a heat-curable epoxy resin composition comprising an epoxy prepolymer and a novel family of aromatic polyamine curing agents. No member of this novel family of curing agents is specifically exemplified in the U.K. patent. The invention provides neat resin formulations having, after cure, improved physical properties, e.g., higher elongation and satisfactory hot/wet modulus. The epoxy compositions of the present invention, cured with filaments, exhibit improved interlaminar toughness and residual compression strength after impact, while maintaining compression strength under hot/wet conditions.

SUMMARY OF THE INVENTION

It is an object of the present invention to provide a fiber resin matrix composition that affords satisfactory compression strength over known matrix formulations, especially under hot/wet conditions, and improved compression strength after impact.

In another aspect, the present invention contemplates fiber-reinforced heat-curable epoxy resin compositions comprising:

(i) an epoxy prepolymer or combination of prepolymers having more than one epoxide group per molecule, and (ii) an amount effective to promote cure of an amine-functional curing agent or combination of curing agents selected from those of the formula:

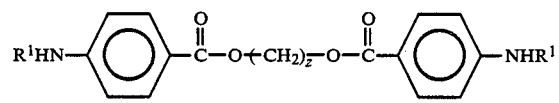

wherein $R^1$ is hydrogen or methyl, and z is an integer of from 2 to 12, preferably 3. Special mention is made of the compound in which $R^1$ is methyl and z is 3.

It is among the features of this aspect of the invention to provide such compositions in filled and/or reinforced, e.g., glass fiber reinforced, embodiments which are useful as prepregs, for example, to make laminates and other structural shapes in accordance with procedures known in this art.

Still another aspect, the present invention provides compositions of epoxy resins and the above-mentioned diamine curing agents which also include a second resin in an amount sufficient to impart improvements in mechanical properties, especially toughness, while preserving substantial resistance to failure under hot/wet conditions. Such resins can be present homogeneously and also in the form known as interpenetrating polymer networks. Particularly useful in this aspect are resins which include repeating units of the formula:

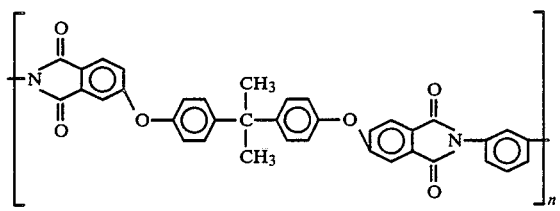

wherein n is a number sufficient to provide a molecular weight of 20,000 to 60,000. Amounts of 5 to 30, preferably 10 to 20 parts by weight per 100 parts by weight of epoxy prepolymer can be used.

DESCRIPTION OF THE PREFERRED EMBODIMENTS

Fillers, pigments, dyes, reinforcements, such as glass fibers or woven cloths, plasticizers, and mixtures thereof, may be added to the epoxy resin—polyamine composition before the reaction in order to modify ultimate properties, in known ways. Applications can also be made by trowelling, brush coating, immersion or dip-coating, spraying and other convenient method. Catalysts, such as boron trifluoride—organic amine adducts, and the reaction product of toluene 2,4-diisocyanate and dimethylamine can also be included, in quantities of from e.g., 0.1 to 5% by weight based on the resin—polyamine, to accelerate curing.

The fiber resin matrix compositions according to the present invention can be prepared by embedding filaments, e.g., glass fibers and/or non-siliceous filaments in a curable resin composition to form a fiber resin matrix which can be manipulated and cured to a solid composite. Particular selection of the filament material, epoxy prepolymer and curing agent, as well as including optional ingredients such as fillers, dyes, catalysts, processing aids, etc., can give a range of curable compositions heretofore unknown in the art and exhibiting improved physical properties over known materials.

Glass filaments useful herein are well known. The non-siliceous filament component may be of any non-glass, non-silicon dioxide-containing material which improves the strength or other physical properties of the curable epoxy resin component (described infra.). Such filaments include, but are not limited to, filaments comprised of carbon, graphite, silicon carbide, boron, aramid, polyester, polyamide, rayon, polybenzimidazole, polybenzothiazole, metal-coated such filaments, for example nickel-coated and/or silver-coated graphite fibers and filaments, or combinations of such filaments. Fibers (woven or non-woven), tows or mats of such filaments, or tapes (unwoven, flat bundles of the unidirectional filaments) may be employed as described. In applications demanding high stiffness to weight ratio or shear strength, carbon fibers, graphite filaments, polyaramid filaments or nickel-plated graphite filaments, as disclosed in assignee's copending application Ser. No. 358,637 are most preferred.

The epoxy resin (i) suitable for the present invention is N,N,N',N'-tetraglycidyl-4,4'-diaminodiphenyl methane.

Figure 1:
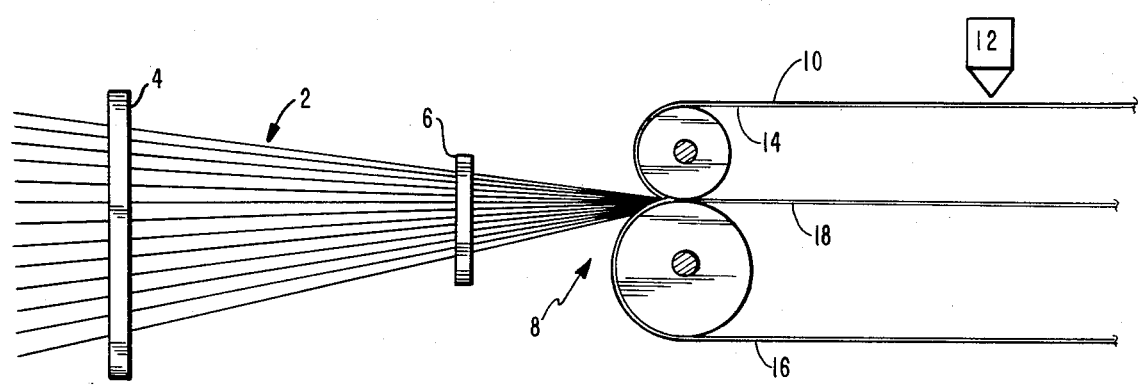
FIG. 1 is a schematic of one method for preparing a fiber resin matrix prepreg tape of the present invention.

One method of forming the fiber matrix composition of the invention is illustrated in the drawings. As seen in FIG. 1, the basic fiber matrix material is produced by delivering fiber 2 through conventional eyeboards 4 and 6 to a pressure roller assembly 8. The resin composition is coated in a layer 10 from a conventional film coating applicator 12 onto a substrate such as release paper 14 and passed through the pressure roller assembly 8. Release paper 16 is also delivered to the pressure roller assembly 8.

The pressure rollers 8 are set at a temperature and pressure for imbedding the fibers 2 in the resin layer 10 to form a fiber matrix composition 18. Practice has taught that a temperature in the range of 190° F. and pressures of one thousand pounds over fifteen inch centers are suitable for producing fiber resin prepreg tape 18.

The fibers 2, the substrate 14 with resin layer 10 and the release paper 16 are delivered to the pressure rollers 8 and passed therethrough at the rate of 5-20 feet/minute.

The feed of fiber 2 and resin layer 10 to the pressure rollers 8 is selected to produce a fiber matrix of about twenty to sixty weight percent resin and about eighty to forty weight percent fiber. For example, one hundred twenty spools of 6K carbon fibers are delivered within a twelve inch width to the pressure rollers 8 with a layer of resin 0.009 to 0.0013 pounds per square foot. The resulting fiber resin matrix 18 results in a generally parallel array of fibers, shown by FIG. 2.

Fillers, pigments, dyes, curing catalysts and other such conventional additives and processing aids may be added to the fiber matrix compositions of the invention before curing to influence the properties of the final resin composite. In addition, polymeric additives such as the butadiene-styrene-acrylonitrile core-shell polymers and the like can be included for their known effects on polymer properties.

The following examples will illustrate the practice of the present invention and are provided by way of demonstration and not by way of limitation.

EXAMPLE 1

Figure 2:
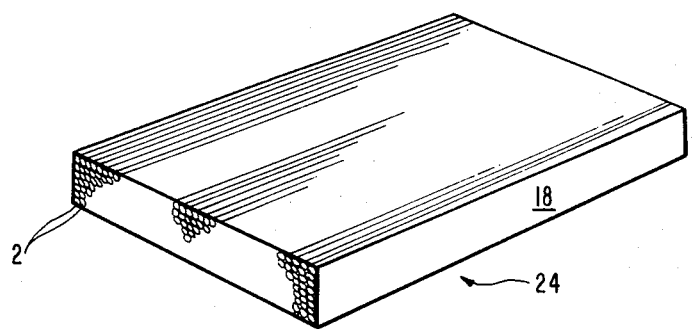
FIG. 2 is an enlarged cross-sectional view of a strip of the fiber resin matrix prepreg tape of the invention.
Figure 3:
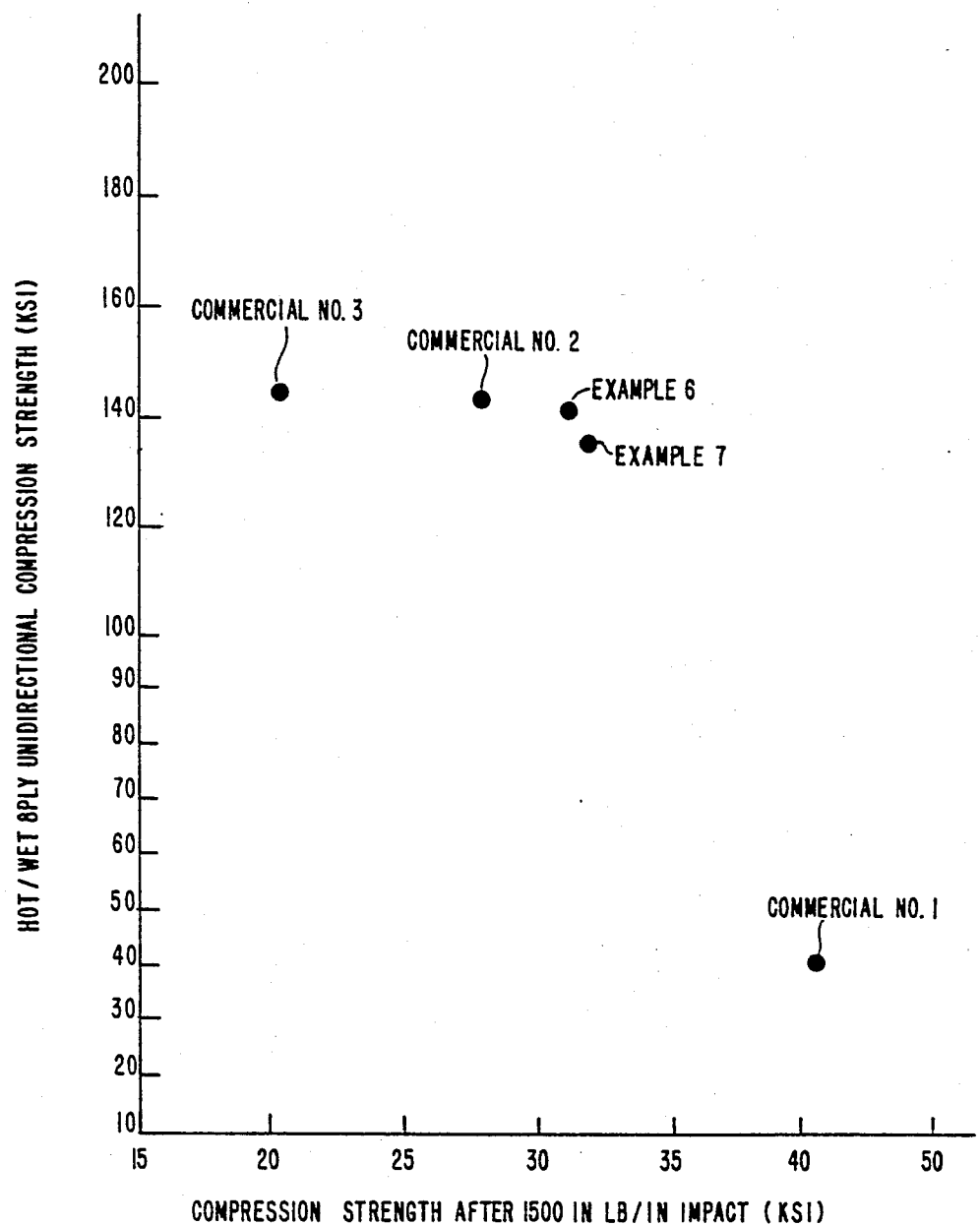
FIG. 3 is a graphical representation comparing hot/wet compressive strength versus dry impact strength for composites according to this invention with state-of-the-art composites.

A resin composition is prepared by mixing the following (by weight)
 (a) N,N,N',N'-tetraglycidyl-4,4'diamino diphenyl methane: 120 parts
 (b) Polyether polyimide resin (General Electric Ultem, Example 11, above): 15 parts
 (c) trimethylene bis-p-aminobenzoate): 48 parts
 (d) Boron trifluoride-ethylamine complex (catalyst): 0.5 parts Using an apparatus shown generally in FIG. 1, prepreg tapes of the structure shown generally in FIG. 2 were prepared with a 35 to 45, preferably 40%, resin/55 to 65, preferably 60%, graphite loading. When this is formed into laminates excellent quality composites are produced. Preferred ranges of compositions are (a), 114–126 parts; (b), 14.25–15.75 parts; (c) 45.6–50.4 parts; and (d), 0.475–0.525 parts.

The above-mentioned patents, applications and publications are incorporated herein by reference. It is seen that the present invention produces articles of manufacture with beneficial properties, making them useful in a variety of applications. Many variations will suggest themselves to those skilled in this art in light of the foregoing detailed description. All such obvious variations are within the full intended scope of the appended claims.

What is claimed is:

1. A fiber resin matrix composition comprised of:
  (a) reinforcing filaments, and
  (b) a heat curable epoxy resin composition formed from the following materials, in parts by weight:
   (i) N,N,N',N'-tetraglycidyl-4,4'-diaminodiphenyl methane, 114–126 parts;
   (ii) a polyetherpolyimide resin of the formula:

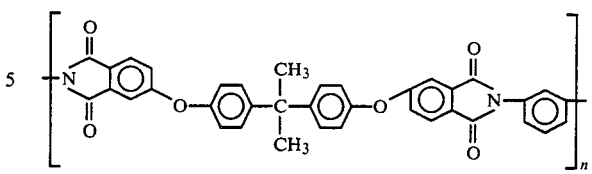

wherein n is an integer sufficient to provide a molecular weight of from 25,000 to 50,000, 14.25–15.75 parts;
   (iii) 1,3-propylene-bis-(p-aminobenzoate 45.6–50.4 parts; and
   (iv) boron trifluoride-organic amine complex, 0.475–0.525 parts.

2. A composition as defined in claim 1 wherein component (b)(i) comprises 120 parts; component (b)(ii) comprises 15 parts; component (b)(iii) comprises 48 parts; and component (b)(iv) comprises 0.5 parts.

3. A fiber resin matrix composition as defined in claim 1 wherein component (a) comprises 55–65 parts by weight and component (b) comprises 35–45 parts by weight per 100 parts by weight of (a) and (b) combined.

4. A fiber resin matrix composition as defined in claim 2 wherein component (a) comprises 60 parts by weight and component (b) comprises 40 parts by weight per 100 parts by weight of (a) and (b) combined.

5. A matrix composition as defined in claim 1 wherein the filaments comprise carbon or graphite filaments.

6. A matrix composition as defined in claim 5 wherein the filaments are graphite filaments and they are in generally parallel alignment.

* * * * *